(12) United States Patent
Efrati

(10) Patent No.: US 11,938,270 B2
(45) Date of Patent: Mar. 26, 2024

(54) ENDOTRACHEAL TUBE AND INTUBATION SYSTEM INCLUDING SAME

(71) Applicant: Hospitech Respiration Ltd., Petach-Tikva (IL)

(72) Inventor: Shai Efrati, Rechovot (IL)

(73) Assignee: Hospitech Respiration Ltd., Kfar-Saba (IL)

(*) Notice: Subject to any disclaimer, the term of this patent is extended or adjusted under 35 U.S.C. 154(b) by 658 days.

(21) Appl. No.: 15/398,773

(22) Filed: Jan. 5, 2017

(65) Prior Publication Data

US 2017/0113011 A1 Apr. 27, 2017

Related U.S. Application Data

(63) Continuation of application No. 12/085,909, filed as application No. PCT/IL2006/001401 on Dec. 5, 2006, now Pat. No. 9,555,205.

(60) Provisional application No. 60/830,111, filed on Jul. 12, 2006, provisional application No. 60/741,900, filed on Dec. 5, 2005.

(51) Int. Cl.
A61M 16/04 (2006.01)

(52) U.S. Cl.
CPC .... *A61M 16/0463* (2013.01); *A61M 16/0434* (2013.01); *A61M 16/0479* (2014.02); *A61M 16/0486* (2014.02); *A61M 2016/0413* (2013.01); *A61M 2205/15* (2013.01);
(Continued)

(58) Field of Classification Search
CPC .......... A61M 16/00; A61M 16/0402; A61M 16/0434; A61M 16/044; A61M 16/0445;
A61M 16/0454; A61M 16/0456; A61M 16/0459; A61M 16/0465; A61M 16/04–0497; A61M 16/0051; A61M 25/10; A61M 2205/15; A61M 2205/32; A61M 2230/005;
(Continued)

(56) References Cited

U.S. PATENT DOCUMENTS 3,504,676 A 6/1970 Lomholt
3,794,036 A 2/1974 Carroll
(Continued)

FOREIGN PATENT DOCUMENTS

CN 1535167 10/2004
DE 4009468 9/1991
(Continued)

OTHER PUBLICATIONS

Communication Pursuant to Article 94(3) EPC dated Jan. 30, 2017 From the European Patent Office Re. Application No. 06780425.2. (4 Pages).
(Continued)

*Primary Examiner* — Margaret M Luarca

(57) ABSTRACT

An endotracheal tube comprises a main lumen for delivering a breathing gas into a lung of a patient, and a cuff, mounted at a distal end of the endotracheal tube, to be located in the subglottal region of the patient. The endotracheal tube also comprises a cuff inflation lumen for inflating the cuff, and at least three additional lumens, other than the main lumen and the cuff inflation lumen, configured for delivering liquid to the subglottal region, for suctioning liquid from the subglottal region, and for venting the subglottal region.

20 Claims, 10 Drawing Sheets

(52) U.S. Cl.
CPC ... *A61M 2205/32* (2013.01); *A61M 2230/005* (2013.01); *A61M 2230/432* (2013.01)

(58) Field of Classification Search
CPC ....... A61M 2016/0027–0042; A61M 16/0479; A61M 16/0463; A61M 16/0486
See application file for complete search history.

(56) References Cited

U.S. PATENT DOCUMENTS

| | | | |
|---|---|---|---|
| 4,159,722 A | 7/1979 | Walker | |
| 4,198,970 A | 4/1980 | Luomanen | |
| 4,305,392 A | 12/1981 | Chester | |
| 4,383,534 A | 5/1983 | Peters | |
| 4,501,273 A | 2/1985 | McGinnis | |
| 4,607,635 A | 8/1986 | Heyden | |
| 4,632,108 A | 12/1986 | Geil | |
| 4,691,701 A | 9/1987 | Williams | |
| 4,770,170 A | 9/1988 | Sato et al. | |
| 4,790,327 A | 12/1988 | Despotis | |
| 4,813,431 A | 3/1989 | Brown | |
| 4,825,862 A | 5/1989 | Sato et al. | |
| 4,850,371 A | 7/1989 | Broadhurst et al. | |
| 4,924,862 A | 5/1990 | Levinson | |
| 4,994,117 A | 2/1991 | Fehder | |
| 5,067,497 A | 11/1991 | Greear et al. | |
| 5,095,896 A | 3/1992 | Omoigui | |
| 5,146,916 A * | 9/1992 | Catalani ................ | A61M 16/04 128/207.14 |
| 5,193,544 A | 3/1993 | Jaffe | |
| 5,197,464 A | 3/1993 | Babb et al. | |
| 5,235,973 A | 8/1993 | Levinson | |
| 5,251,619 A | 10/1993 | Lee | |
| 5,264,697 A | 11/1993 | Nakagawa et al. | |
| 5,285,778 A | 2/1994 | Mackin | |
| 5,291,879 A | 3/1994 | Babb et al. | |
| 5,354,267 A | 10/1994 | Niermann et al. | |
| 5,360,003 A | 11/1994 | Capistrano | |
| 5,360,414 A | 11/1994 | Yarger | |
| 5,361,753 A | 11/1994 | Pothmann et al. | |
| 5,372,131 A * | 12/1994 | Heinen, Jr. ....... | A61M 16/0479 128/207.14 |
| 5,400,771 A | 3/1995 | Pirak et al. | |
| 5,445,144 A | 8/1995 | Wodicka et al. | |
| 5,445,161 A | 8/1995 | Huang | |
| 5,499,625 A * | 3/1996 | Frass .................... | A61M 16/04 128/200.26 |
| 5,579,762 A | 12/1996 | Lee | |
| 5,582,166 A | 12/1996 | Lee | |
| 5,582,167 A | 12/1996 | Joseph | |
| 5,622,182 A | 4/1997 | Jaffe | |
| 5,669,380 A | 9/1997 | Garry et al. | |
| 5,697,365 A | 12/1997 | Pell | |
| 5,752,921 A | 5/1998 | Orr | |
| 5,765,559 A | 6/1998 | Kim | |
| 5,785,051 A | 7/1998 | Lipscher et al. | |
| 5,791,341 A | 8/1998 | Bullard | |
| 5,803,078 A | 9/1998 | Brauner | |
| 5,819,723 A | 10/1998 | Joseph | |
| 5,819,727 A | 10/1998 | Linder | |
| 5,919,183 A | 7/1999 | Field | |
| 5,937,861 A | 8/1999 | Augustine | |
| 6,059,732 A | 5/2000 | Orr et al. | |
| 6,062,223 A | 5/2000 | Palazzo et al. | |
| 6,071,237 A | 6/2000 | Weil et al. | |
| 6,098,617 A | 8/2000 | Connell | |
| 6,135,105 A | 10/2000 | Lampotang et al. | |
| 6,315,739 B1 | 11/2001 | Merilainen et al. | |
| 6,450,164 B1 | 9/2002 | Banner et al. | |
| 6,474,332 B2 | 11/2002 | Arndt | |
| 6,550,475 B1 | 4/2003 | Oldfield | |
| 6,568,388 B2 | 5/2003 | Christopher | |
| 6,568,393 B2 | 5/2003 | Christopher | |
| 6,571,796 B2 | 6/2003 | Banner et al. | |
| 6,843,250 B2 | 1/2005 | Efrati | |
| 7,036,501 B2 | 5/2006 | Wall | |
| 7,171,962 B1 | 2/2007 | Bloem | |
| 7,278,420 B2 | 10/2007 | Ganesh et al. | |
| 7,360,541 B2 | 4/2008 | Dhuper et al. | |
| 7,503,328 B2 | 3/2009 | Kolobow et al. | |
| 7,954,488 B2 | 6/2011 | Munn | |
| 8,424,529 B2 | 4/2013 | Efrati et al. | |
| 9,004,069 B2 | 4/2015 | Efrati et al. | |
| 9,555,205 B2 * | 1/2017 | Efrati ................ | A61M 16/0486 |
| 2002/0014238 A1 * | 2/2002 | Kotmel ............ | A61M 16/0459 128/204.18 |
| 2002/0078962 A1 | 6/2002 | Nash et al. | |
| 2003/0051733 A1 | 3/2003 | Kotmel et al. | |
| 2003/0145860 A1 | 8/2003 | Johnson | |
| 2003/0172925 A1 | 9/2003 | Zocca et al. | |
| 2004/0123867 A1 * | 7/2004 | Efrati ................ | A61M 16/0479 128/207.14 |
| 2004/0129272 A1 | 7/2004 | Ganesh et al. | |
| 2005/0039754 A1 | 2/2005 | Simon | |
| 2005/0045180 A1 | 3/2005 | Heinonen | |
| 2005/0279354 A1 | 12/2005 | Deutsch et al. | |
| 2006/0081255 A1 | 4/2006 | Miller et al. | |
| 2007/0044807 A1 | 3/2007 | Madsen et al. | |
| 2007/0137651 A1 | 6/2007 | Glassenberg et al. | |
| 2008/0000481 A1 | 1/2008 | Ganesh et al. | |
| 2008/0283052 A1 * | 11/2008 | Young ............... | A61M 16/0431 128/207.15 |
| 2009/0013995 A1 | 1/2009 | Williams | |
| 2009/0038620 A1 | 2/2009 | Efrati | |
| 2009/0229605 A1 | 9/2009 | Efrati et al. | |
| 2011/0100373 A1 | 5/2011 | Efrati et al. | |
| 2012/0000471 A1 | 1/2012 | Harrington et al. | |
| 2015/0209532 A1 | 7/2015 | Efrati et al. | |

FOREIGN PATENT DOCUMENTS

| | | |
|---|---|---|
| DE | 19734821 | 2/1999 |
| EP | 0347101 | 12/1989 |
| EP | 0640357 | 3/1995 |
| EP | 0728493 | 8/1996 |
| EP | 1418969 | 5/2004 |
| GB | 1414344 | 11/1975 |
| HU | 179929 | 5/1982 |
| HU | 206458 | 3/1992 |
| HU | P0003171 | 2/2001 |
| HU | P0104580 | 12/2002 |
| IL | 142228 | 4/2007 |
| JP | 06-504454 | 5/1994 |
| JP | 09-313609 | 9/1997 |
| JP | 10-165505 | 6/1998 |
| JP | 10-337326 | 12/1998 |
| JP | 10-504733 | 12/1998 |
| JP | 2001-513372 | 9/2001 |
| JP | 2002-210014 | 7/2002 |
| JP | 2004-136118 | 5/2004 |
| JP | 2004-528887 | 9/2004 |
| WO | WO 92/07602 | 5/1992 |
| WO | WO 95/33506 | 12/1995 |
| WO | WO 99/029358 | 6/1999 |
| WO | WO 00/048510 | 8/2000 |
| WO | WO 02/076279 | 10/2002 |
| WO | WO 03/101516 | 12/2003 |
| WO | WO 2004/030527 | 4/2004 |
| WO | WO 2005/112796 | 12/2005 |
| WO | WO 2005/118039 | 12/2005 |
| WO | WO 2007/023492 | 3/2007 |
| WO | WO 2007/066332 | 6/2007 |

OTHER PUBLICATIONS

Hearing Notice dated Jul. 26, 2019 From the Government of India, Patent Office, Intellectual Property Building Re. Application No. 05711/DELNP/2008. (3 Pages).

Communication Relating to the Results of the Partial International Search dated Jan. 25, 2007 From the International Searching Authority Re.: Application No. PCT/IL2006/000974.

(56) References Cited

OTHER PUBLICATIONS

Communication Relating to the Results of the Partial International Search dated Mar. 27, 2007 From the International Searching Authority Re.: Application No. PCT/IL2006/001401.
International Preliminary Report on Patentability dated May 6, 2008 From the International Preliminary Examining Authority Re.: Application No. PCT/IL2006/001401.
International Preliminary Report on Patentability dated Mar. 27, 2008 From the International Preliminary Examining Authority Re.: Application No. PCT/IL2006/001401.
Applicant-Initiated Interview Summary dated Sep. 12, 2013 From the US Patent and Trademark Office Re. U.S. Appl. No. 12/085,909.
Communication Pursuant to Article 94(3) EPC dated Aug. 2, 2011 From the European Patent Office Re. Application No. 06821620.9.
Communication Pursuant to Article 94(3) EPC dated Aug. 7, 2009 From the European Patent Office Re.: Application No. 02707077.0.
Communication Pursuant to Article 94(3) EPC dated Dec. 13, 2011 From the European Patent Office Re. Application No. 06821620.9.
Corrected Written Opinion dated Jan. 6, 2010 From the Intellectual Property Office of Singapore Issued by the Danish Patent and Trademark Office Re.: Application No. SG200804735-9.
Examination Report dated Dec. 4, 2009 From the Intellectual Property Office of New Zealand Re.: Application No. 566767.
Examination Report dated Oct. 8, 2010 From the Intellectual Property Office of New Zealand Re. Application No. 588268.
Examination Report dated Sep. 13, 2007 From the Government of India, Patent Office Re.: Application No. 982/MUMNP/2003.
Examination Report dated Mar. 15, 2016 From the Government of India, Patent Office, Intellectual Property Building Re. Application No. 05711/DELNP/2008.
Examination Report dated Oct. 20, 2010 From the Intellectual Property Office of New Zealand Re.: Application No. 566767.
Examination Report dated Dec. 21, 2009 From the Intellectual Property Office of New Zealand Re.: Application No. 569496.
Examination Report dated Oct. 22, 2013 From the Instituto Mexicano de la Propiedad Industrial Re. Application No. MX/a/2008/007080 and Its Translation Into English.
Examination Report dated Nov. 24, 2009 From the Intellectual Property Office of New Zealand Re.: Application No. 569496.
Examination Report dated Jun. 28, 2013 From the Instituto Mexicano de la Propiedad Industrial Re. Application No. MX/a/2008/002397 and Its Translation Into English.
Examiner's Report dated Feb. 20, 2012 From the Australian Government, IP Australia Re. Application No. 2006282737.
Examiner's Report dated Sep. 23, 2005 From the Australian Government, IP Australia Re.: Application No. 2002241229.
Examiner's Report dated Sep. 28, 2006 From the Australian Government, IP Australia Re.: Application No. 2002241229.
International Preliminary Report on Patentability dated Dec. 19, 2007 From the International Preliminary Examining Authority Re.: Application No. PCT/IL2006/000974.
International Search Report dated May 2, 2003 From the International Searching Authority Re.: Application No. PCT/IL02/00230.
International Search Report dated May 11, 2007 From the International Searching Authority Re.: Application No. PCT/IL2006/000974.
International Search Report dated Aug. 14, 2007 From the International Searching Authority Re.: Application No. PCT/IL2006/001401.
Interview Summary dated Aug. 2, 2011 From the US Patent and Trademark Office Re. U.S. Appl. No. 11/990,694.
Justification dated Jan. 12, 2009 From the Polish Industrial Property Office Re.: Application No. P-373498 and Its Translation Into English.
Notice of Allowance and Fee(s) Due dated Sep. 9, 2004 From The US Patent and Trademark Office Re.: U.S. Appl. No. 10/471,777.
Notice of Reexamination dated Aug. 12, 2015 From the Patent Reexamination Board of State Intellectual Property Office of the People's Republic of China Re. Application No. 200680052386.4 and Its Translation Into English.
Notice of Reexamination dated Dec. 26, 2014 From the Patent Reexamination Board of State Intellectual Property Office of the People's Republic of China Re. Application No. 200680052386.4 and Its Translation Into English.
Office Action dated Oct. 6, 2011 From the Israel Patent Office Re. Application No. 189689 and Its Translation Into English.
Office Action dated Sep. 16, 2010 From the Hungarian Patent Office (HPO) Re. Application No. P0400315.
Office Action dated Apr. 21, 2016 From the State Intellectual Property Office of the People's Republic of China Re. Application No. 200680052386.4 and Its Translation Into English.
Office Action dated May 26, 2010 From the Israel Patent Office Re. Application No. 189689 and Its Translation Into English.
Office Action dated Jul. 27, 2010 From the Israel Patent Office Re. Application No. 192006 and Its Translation Into English.
Office Action dated Mar. 28, 2012 From the Israel Patent Office Re. Application No. 192006 and Its Translation Into English.
Office Action dated Jan. 30, 2014 From the Israel Patent Office Re. Application No. 189689 and Its Translation Into English.
Official Action dated Feb. 1, 2016 From the US Patent and Trademark Office Re. U.S. Appl. No. 12/085,909.
Official Action dated May 3, 2011 From the US Patent and Trademark Office Re. U.S. Appl. No. 11/990,694.
Official Action dated Oct. 5, 2010 From the US Patent and Trademark Office Re. U.S. Appl. No. 11/990,694.
Official Action dated Oct. 9, 2014 From the US Patent and Trademark Office Re. U.S. Appl. No. 12/085,909.
Official Action dated Apr. 11, 2013 From the US Patent and Trademark Office Re. U.S. Appl. No. 12/984,673.
Official Action dated Oct. 11, 2011 From the US Patent and Trademark Office Re. U.S. Appl. No. 12/984,673.
Official Action dated Sep. 14, 2011 From the US Patent and Trademark Office Re. U.S. Appl. No. 12/085,909.
Official Action dated Apr. 16, 2015 From the US Patent and Trademark Office Re. U.S. Appl. No. 12/085,909.
Official Action dated Mar. 16, 2012 From the US Patent and Trademark Office Re. U.S. Appl. No. 12/085,909.
Official Action dated Dec. 17, 2013 From the US Patent and Trademark Office Re. U.S. Appl. No. 12/085,909.
Official Action dated Dec. 22, 2011 From the US Patent and Trademark Office Re. Application No. U.S. Appl. No. 11/990,694.
Official Action dated Jul. 23, 2012 From the US Patent and Trademark Office Re. U.S. Appl. No. 12/984,673.
Official Action dated Aug. 25, 2014 From the US Patent and Trademark Office Re. U.S. Appl. No. 12/984,673.
Official Action dated Oct. 25, 2012 From the US Patent and Trademark Office Re. U.S. Appl. No. 12/085,909.
Official Action dated Jun. 28, 2013 From the US Patent and Trademark Office Re. U.S. Appl. No. 12/085,909.
Official Decision to Grant dated Mar. 4, 2014 From the Japanese Patent Office Re. Application No. 2008-544000 and Its Translation Into English.
Patent Examination Report dated Aug. 1, 2013 From the Australian Government, IP Australia Re. Application No. 2006322905.
Patent Examination Report dated Jun. 21, 2012 From the Australian Government, IP Australia Re. Application No. 2006322905.
Patent Examination Report dated Oct. 23, 2012 From the Australian Government, IP Australia Re. Application No. 2006282737.
Requisition by the Examiner dated Apr. 4, 2013 From the Canadian Intellectual Property Office Re. Application No. 2,631,516.
Requisition by the Examiner dated Aug. 5, 2013 From the Canadian Intellectual Property Office Re. Application No. 2,619,687.
Requisition by the Examiner dated Nov. 21, 2013 From the Canadian Intellectual Property Office Re. Application No. 2,631,516.
Requisition by the Examiner dated Nov. 27, 2012 From the Canadian Intellectual Property Office Re. Application No. 2,619,687.
Search Report and Written Opinion dated Feb. 9, 2009 From the Intellectual Property Office of Singapore Issued by the Danish Patent and Trademark Office Re.: Application No. 200804735-9.
Search Report dated Nov. 7, 2008 From the Intellectual Property Office of Singapore Issued by the Australian Patent Office Re.: Application No. 200801440-9.

(56) References Cited

OTHER PUBLICATIONS

Summons to Attend Oral Proceedings Pursuant to Rule 115(1) EPC dated Oct. 11, 2012 From the European Patent Office Re. Application No. 06821620.9.
Supplementary European Search Report dated Jun. 4, 2009 From the European Patent Office Re.: Application No. EP 02707077.
Translation of Notice of the Reason for Rejection dated Jun. 17, 2013 From the Korean intellectual Property Office Re. Application No. 2008-7006807.
Translation of Decision on Rejection Dated Apr. 2, 2013 From the State Intellectual Property Office of the People's Republic of China Re. Application No. 200680052386.4.
Translation of Notice of Reason for Rejection dated Sep. 21, 2012 From the Japanese Patent Office Re. Application No. 2008-544000.
Translation of Notice of Reason for Rejection dated Nov. 25, 2011 From the Japanese Patent Office Re. Application No. 2008-544000.
Translation of Notice of Reason for Rejection dated Jul. 26, 2011 From the Japanese Patent Office Re. Application No. 2008-527592.
Translation of Notice of the Reason for Rejection dated Nov. 8, 2012 From the Korean Intellectual Property Office Re. Application No. 2008-7006807.
Translation of Notification of Reasons for Refusal dated Mar. 25, 2008 From the Japanese Patent Office Re.: Application No. 2002-574801.
Translation of Office Action dated Dec. 3, 2012 From the State Intellectual Property Office of the People's Republic of China Re. Application No. 200680052386.4.
Translation of Office Action dated May 3, 2012 From the State Intellectual Property Office of the People's Republic of China Re. Application No. 201010552126.1.
Translation of Office Action dated Oct. 10, 2012 From the State Intellectual Property Office of the People's Republic of China Re. Application No. 201010552126.1.
Translation of Office Action dated Nov. 16, 2011 From the State Intellectual Property Office of the People's Republic of China Re. Application No. 200680039482.5.
Translation of Office Action dated Jan. 19, 2011 From the State Intellectual Property Office of the People's Republic of China Re. Application No. 200680052386.4.
Translation of Office Action dated Jun. 24, 2011 From the State Intellectual Property Office of the People's Republic of China Re. Application No. 201010552126.1.
Translation of Office Action dated May 25, 2010 From the State Intellectual Property Office of the People's Republic of China Re. Application No. 200680039482.5.
Translation of Office Action dated Mar. 28, 2012 From the State Intellectual Property Office of the People's Republic of China Re. Application No. 200680052386.4.
Translation of Reason for Rejection dated Jun. 28, 2013 From the Japanese Patent Office Re. Application No. 2008-544000.
Translation of the Essential Parts of the Official Letter dated Aug. 3, 2012 From the Patent Office of the Czech Republic Re. Application No. 2003-2785.
Translation of the Office Action dated Oct. 31, 2005 From the State Intellectual Property Office of the People's Republic of China Re.: Application No. 02801194.5.
Written Opinion dated Nov. 7, 2008 From the Intellectual Property Office of Singapore Issued by the Australian Patent Office Re.: Application No. 200801440-9.
Written Opinion dated Feb. 9, 2009 From the Intellectual Property Office of Singapore Issued by the Danish Patent and Trademark Office Re.: Application No. SG200804735-9.
Written Opinion dated May 11, 2007 From the International Searching Authority Re.: Application No. PCT/IL2006/000974.
Written Opinion dated Aug. 14, 2007 From the International Searching Authority Re.: Application No. PCT/IL2006/001401.
Written Opinion dated Jun. 19, 2009 From the Intellectual Property Office of Singapore Issued by the Australian Government, IP Australia Re.: Application No. SG 200801440-9.
Written Opinion dated Sep. 28, 2009 From the Intellectual Property Office of Singapore Issued by the Danish Patent and Trademark Office Re.: Application No. SG 200804735-9.
Efrati et al. "Optimization of Endotracheal Tube Cuff Filling by Continuous Upper Airway Carbon Dioxide Monitoring", Anesthesia & Analgesia, 101(4): 1081-1088, 2005.
Official Action dated Feb. 4, 2019 From the US Patent and Trademark Office Re. U.S. Appl. No. 14/684,385. (30 pages).
Examination Report Under Sections 12 & 13 of the Patents Act, 1970 and the Patents Rules, 2003 dated Feb. 14, 2017 From the Government of India, Patent Office, Intellectual Property Building Re. Application No. 1425/CHENP/2008. (7 Pages).
Restriction Official Action dated Oct. 19, 2018 From the US Patent and Trademark Office Re. U.S. Appl. No. 14/684,385. (6 Pages).
Official Action dated Oct. 24, 2019 From the US Patent and Trademark Office Re. U.S. Appl. No. 14/684,385. (13 pages).

* cited by examiner

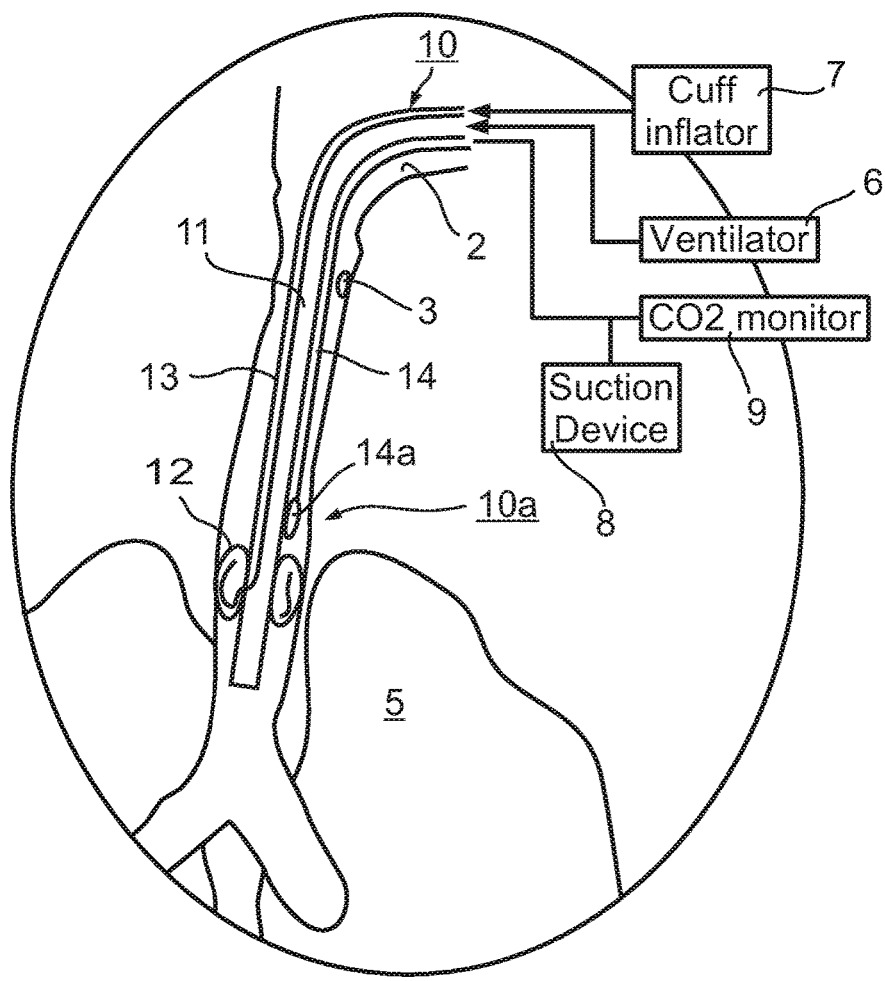
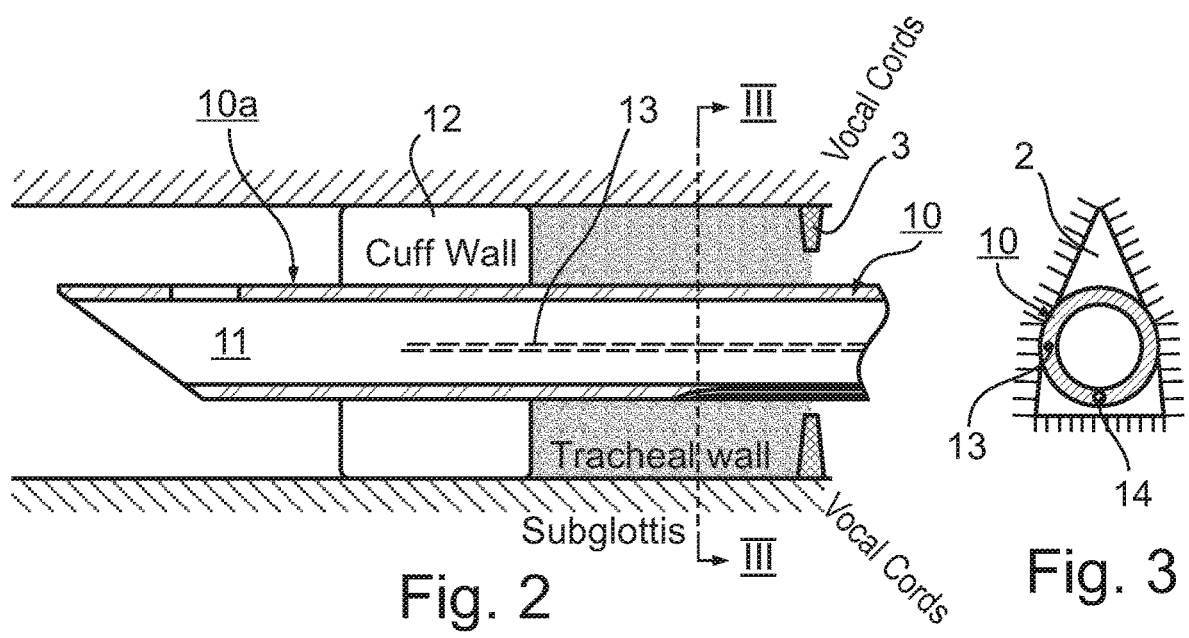
Fig. 1
Fig. 2
Fig. 3

ENDOTRACHEAL TUBE AND INTUBATION
SYSTEM INCLUDING SAME

RELATED APPLICATIONS

This application is a continuation of U.S. patent application Ser. No. 12/085,909 filed Jun. 2, 2008, which is a National Phase of PCT Patent Application No. PCT/IL2006/001401 having International Filing Date of Dec. 5, 2006, which claims the benefit of U.S. Provisional Patent Application Nos. 60/830,111 filed on Jul. 12, 2006 and 60/741,900 filed on Dec. 5, 2005. The contents of the above applications are all incorporated by reference as if fully set forth herein in their entirety.

FIELD AND BACKGROUND OF THE INVENTION

The present invention relates to endotracheal tubes for mechanically ventilating patients, and also to an intubation system including such tubes.

In the medical treatment of patients requiring breathing assistance, it is frequently necessary to insert an endotracheal tube into the trachea of the patient, by way of the mouth or nose and to connect the tube to a ventilator which periodically forces air into the lungs through the tube. The inner or distal end of the tube is typically provided with an inflatable cuff which is inflated into contact with the interior wall of the trachea.

In using such endotracheal tubes, however, problems arise with respect to bodily secretions which pass progressively between the inner surface of the trachea and the outer surface of the cuff. The evacuation of secretions accumulated in the subglottal region above the cuff is required to prevent a ventilator-associated lung infection, commonly called VAP or Ventilator Associated Pneumonia. Attempts have been made in the past to overcome these problems by regulating cuff pressure and/or by suctioning secretions from between the trachea's wall and the endotracheal tube.

The removal of such secretions by suction generally requires the insertion into the subglottal region of an external lumen having a suction inlet port located above the sealing cuff. Another alternative is to use a suction lumen integrally formed in the wall of the endotracheal tube. In either case, the suction lumen is connected to a negative pressure source, thus drawing out secretions within the subglottal region.

However, there is a tendency for the suction lumen to become blocked, particularly during long-term intubation. Attempts have made to prevent or reduce such suction lumen blockage by irrigating the suction channel between successive suctions. Such attempts, however, have frequently been unsuccessful, thereby subjecting the patient to an increase in the risk of lung infection.

SUMMARY OF THE INVENTION

An object of the present invention is to provide an endotracheal tube, and also an intubation system, having advantages in the above respects. Another object of the invention is to provide such a tube and intubation system which reduces the chances of blockage of the suction inlet port of the suction lumen, and more effectively evacuates secretions and/or rinsing fluid from the subglottal region during the mechanical ventilation of the patient.

In studying the problem to be overcome by the present invention, it was noted that the blockage of the suction lumen during the mechanical ventilation of the patient was frequently caused by the movement of a portion of the cuff, or by tracheal mucosal tissue of the patient, over the suction inlet port during the negative pressure condition in the suction lumen. It was accordingly found that by forming the distal end of the endotracheal tube with an outer surface configuration effective to prevent blockage of the suction inlet port by the cuff, or by tracheal mucosal tissue of the patient, the secretions, and/or rinsing fluid, could be more effectively removed from the subglottal region during the mechanical ventilation of the patient with reduced danger of blockage of the suction lumen.

According to one aspect of the present invention, therefore, there is provided an endotracheal tube for mechanically ventilating patients, including a distal end for insertion into the patient's airway, past the vocal chords, through the subglottal region, and into the patient's lung; and a proximal end for connection to a mechanical ventilator; a cuff at the distal end of the endotracheal tube and also to be located in the subglottal region of the patient below the vocal chords; an inflating lumen for inflating the cuff; and a suction lumen having a suction inlet port leading from the outer surface of the endotracheal tube, and to be located in the subglottal region, for evacuating secretions and/or rinsing fluid from the subglottal region during the mechanical ventilation of the patient; characterized in that the distal end of the endotracheal tube is formed with an outer surface configuration effective to prevent blockage of the suction inlet port by the cuff or by tracheal mucosal tissue of the patient during a negative pressure condition in the suction lumen.

In studying the above problem, it was further noted that the negative pressure exerted by the suction lumen caused the creation of a confined space between the vocal cords and the upper side of the cuff, causing the adhesion of cuff or tissue to the suction port. It was accordingly found that by venting the subglottal space with an external or embedded lumen, blockage of the suction inlet port by the cuff, or by tracheal mucosal tissue of the patient and or the secretions, could be more effectively prevented during the mechanical ventilation of the patient.

According to further features in the preferred embodiments of the invention described below, the endotracheal tube comprises a venting lumen leading from the outer surface of the endotracheal tube and also to be located in the patient's subglottal region, for venting the subglottal region to the atmosphere to prevent the creation of vacuum within subglottal space.

According to further features in some described preferred embodiments, the outer surface configuration of the endotracheal tube includes a protuberance adjacent to the suction inlet port and projecting radially outwardly of the outer surface of the endotracheal tube at the suction inlet port effective to prevent such blockage of the suction inlet port. In one described embodiment, the protuberance is integrally formed in the wall of the endotracheal tube as a thickened portion thereof, and in another described embodiment, it is in the form of an inflatable element carried by the wall of the endotracheal tube.

In the described preferred embodiments, the venting lumen is used intermittently for venting and for analyzing air leaked from the lungs, particularly the $CO_2$, within the subglottal region.

In some described embodiments, the proximal end of the suction lumen is constructed for selective connection to a suction source, or to a rinsing-fluid source for circulating a rinsing fluid through the subglottal region. In such embodiments, therefore, the suction lumen is also used as the rinsing-fluid lumen. Other embodiments are described, however, wherein separate suction and rinsing-fluid lumens are provided in the endotracheal tube.

According to another aspect of the present invention, therefore, there is provided an endotracheal tube for mechanically ventilating patients, including: a distal end for insertion into the patient's airway, past the vocal chords, through the subglottal region, and into the patient's lung, and a proximal end for connection to a mechanical ventilator; a cuff at the distal end of the endotracheal tube to be located in the subglottal region of the patient below the vocal chords; an inflating lumen for inflating the cuff; a suction lumen integrally formed in a wall of the endotracheal tube and having a suction inlet port located for evacuating secretions and/or rinsing fluid from the subglottal region during the ventilation of the patient; and a rinsing lumen integrally formed in a wall of the tracheal tube and having a rinsing outlet port to be located in the patient's subglottal region for circulating a rinsing fluid through the subglottal region to be removed by the suction lumen.

In the described preferred embodiment, the endotracheal tube further comprises a venting lumen integrally formed in a wall of the endotracheal tube and having an air suction inlet located for pumping air into a $CO_2$ analyzer or for venting the subglottal space during suction of secretions to prevent under pressurized vacuum conditions in the subglottal space.

According to further features in that described preferred embodiment, the outer wall of the endotracheal tube further includes at least one recess extending at one side of the suction and rinsing lumens from the proximal end of the endotracheal tube to the distal end to be located in the patient's subglottal region, the suction inlet port and the rinsing outlet port being located within the recess such as to reduce the possibility of blockage of the suction inlet port by the cuff or by endotracheal mucosal tissue of the patient during a negative pressure condition in the suction lumen.

Preferably, the outer wall of the endotracheal tube includes two of the recesses straddling the suction and rinsing lumens, there being a suction inlet port and a rinsing-liquid outlet port in each of the recesses.

As will be described more particularly below, endotracheal tubes constructed in accordance with the foregoing features more effectively evacuate secretions and/or rinsing fluid from the subglottal region during the mechanical ventilation of the patient, and prevent blockage of the suction inlet port by the cuff, or by tracheal mucosal tissue of the patient, during the negative pressure condition in the suction lumen.

Further features and advantages of the invention will be apparent from the description below.

BRIEF DESCRIPTION OF THE SEVERAL VIEWS OF THE DRAWINGS

The invention is herein described, by way of example only, with the reference to the accompanying drawings, wherein:

FIG. 1 diagrammatically illustrates one form of prior art intubation system to which the present invention relates;

FIG. 2 is an enlarged fragmentary view illustrating the distal end of the endotracheal tube used in the system of FIG. 1, and particularly the subglottal region through which the tube passes;

FIG. 3 is a transverse sectional view along line III-III of FIG. 2;

Figure 4:
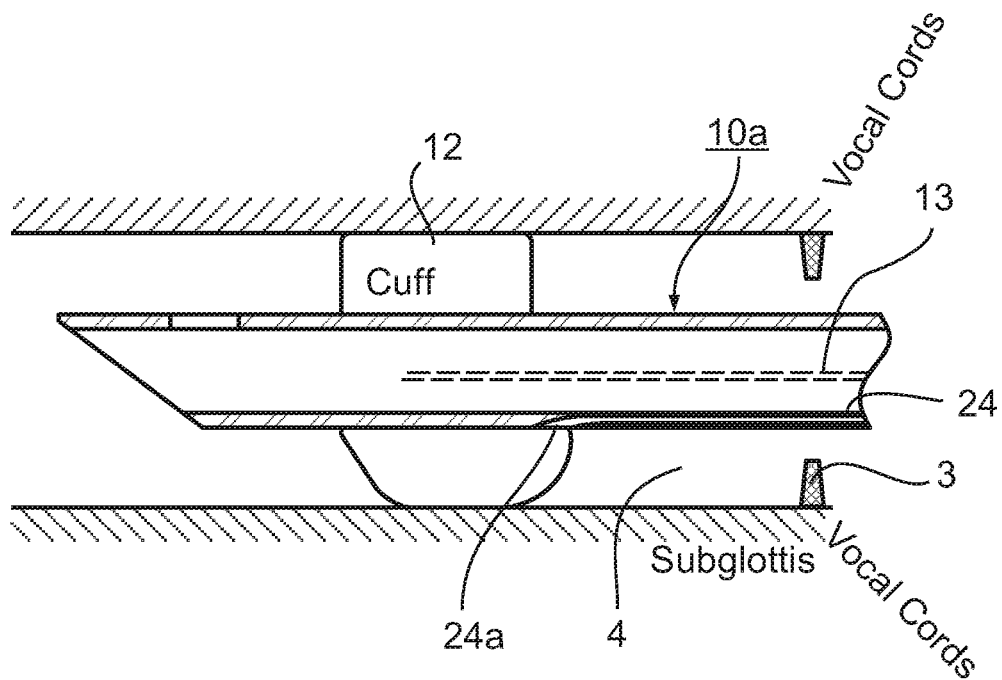
FIGS. 4 and 5 are fragmentary views illustrating two ways in which it was found that the suction lumen frequently becomes blocked during the mechanical ventilation of a patient, thereby preventing evacuation of the secretions from the subglottal region.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF SPECIFIC EMBODIMENTS OF THE INVENTION

The Intubation System of FIGS. 1-5

The preferred embodiments of the present invention to be described below relate primarily to the type of intubation system for mechanically ventilating patients as illustrated in FIGS. 1-3. Such a system utilizes an endotracheal tube, generally designated 10, having a distal end 10a for insertion into the patient's airway 2, past the vocal chords 3, through the subglottal region 4 and into the patient's lungs 5. The proximal end 10b of endotracheal tube 10 is connectable to a mechanical ventilator 6, as well as to a number of control devices as will be described more particularly below.

As indicated earlier, such endotracheal tubes generally include a main lumen 11 for ventilating the patient, and a cuff 12 at the distal end 10a of the tube to be located in the subglottal region 4 of the patient, below the vocal chords. Such tubes also include an inflating lumen 13 extending through the tube for inflating the cuff by a cuff inflator 7 at the proximal end 10b of the tube; and a suction lumen 14 having an inlet port 14a leading from the outer surface of the endotracheal tube, and to be located in the subglottal region 4. Suction lumen 14 is connected, at the proximal end 10 of the endotracheal tube, to a suction device 8 or to a wall provided vacuum port for evacuating secretions from the subglottal region during the mechanical ventilation of the patient. In an embodiment of the invention described below, the subglottal region is also irrigated with a rinsing fluid, in which case suction lumen 14 would be used for evacuating the rinsing fluid introduced into the subglottal region as well as the secretions from the subglottal region.

In some intubation systems, the proximal end of suction lumen 14 may be connected either to a suction device 8, or to a monitor 9 for monitoring the composition, particularly the $CO_2$ content, of the air from the lungs removed via the suction lumen 14. Monitoring the composition of the exhaled air can be used for controlling the cuff-inflation pressure in order to minimize leakage while at the same time avoiding damage to the patient's airway.

Figure 5:
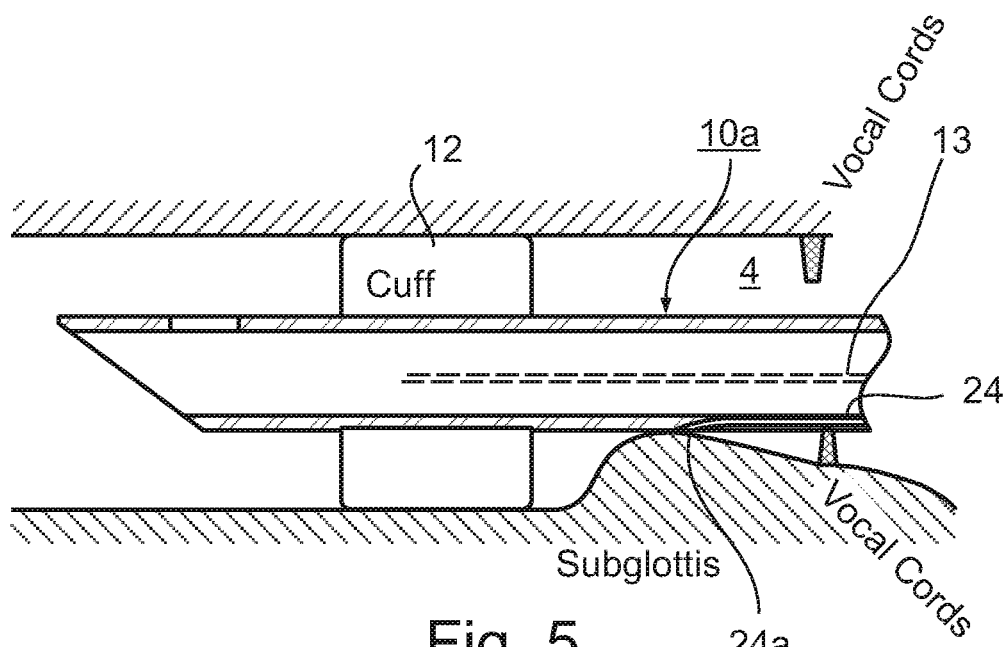

As indicated earlier, the evacuation of secretions via the suction lumen 14 was frequently hindered by blockage of the suction lumen particularly during the long-term intubation. It was found that this was generally caused by blockage of the suction inlet port 14a either by the cuff 12 (as shown in FIG. 4), or by tracheal mucosal tissue of the patient, as shown in FIG. 5, during the negative-pressure condition of the suction lumen.

Figure 6:
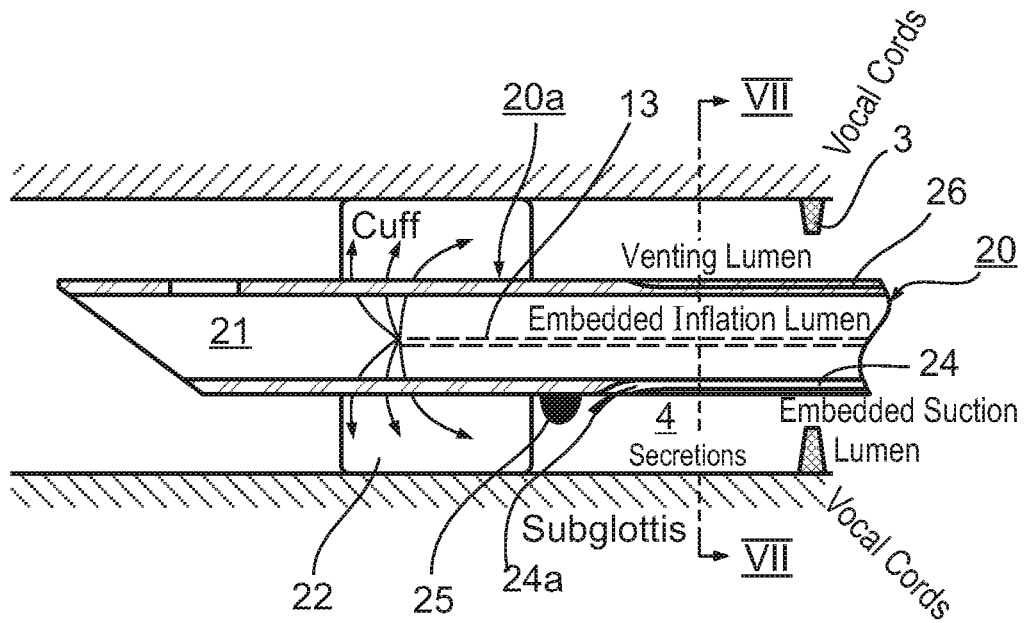
FIG. 6 illustrates one construction of the endotracheal tube in accordance with the present invention to prevent blockage of the suction lumen.
Figure 7:
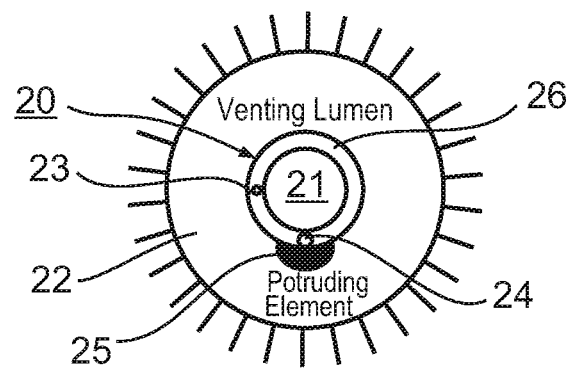
FIG. 7 is a transverse sectional view along lines VII-VII of FIG. 6.

The Embodiment of FIGS. 6 and 7

FIGS. 6 and 7 illustrate one embodiment of an endotracheal tube, generally designated 20, particularly its distal end 20a, constructed in accordance with the present invention for avoiding the above problems. Endotracheal tube 20 includes the usual main lumen 21, cuff 22, and inflation lumen 23 for inflating the cuff. It further includes a suction lumen 24 having a suction inlet port 24a leading from the outer surface of the tube and to be located in the subglottal region, as described above with respect to FIGS. 1-3, for evacuating secretions and/or rinsing fluid from the subglottal region during the mechanical ventilation of the patient.

According to the present invention, the distal end 20a of the endotracheal tube 20 is formed with an outer configuration effective to prevent blockage of the suction inlet port 24a by the cuff 22, or by tracheal mucosal tissue of the patient, during a negative-pressure condition in the suction lumen.

In the embodiment of the invention illustrated in FIGS. 6 and 7, the outer surface of the endotracheal tube is formed with a protuberance 25 adjacent to the suction inlet port 24a and projecting radially outwardly of the outer surface of the tube at the section inlet port, such as to be effective to prevent blockage of the suction inlet port either by cuff 22, or tracheal mucosal tissue within airway 2 of the patient, during a negative pressure condition in the suction lumen.

In the embodiment of the invention illustrated in FIGS. 6 and 7, the protuberance is integrally formed in the wall of the endotracheal tube 20 as a thickened portion thereof and is located in the space between the suction inlet port 24a and the cuff 22. Preferably, the protuberance should have a rounded outer surface projecting radially outwardly of the suction inlet port 24a so as to prevent blockage of that port either by the cuff 22 or by tracheal mucosal tissue.

The endotracheal tube illustrated in FIGS. 6 and 7 includes a further feature, namely a venting lumen 26 integrally formed with, and extending through, the wall of the endotracheal tube 20 for venting the subglottal region to the atmosphere. Such a venting lumen thereby prevents an undue build-up of negative pressure within the subglottal region 4 such that the suction inlet port 24a of the suction lumen 24 may become blocked by the cuff 22 or by tracheal mucosal tissue.

As will be described below, venting lumen 26 may also be also be used for monitoring the composition, particularly the $CO_2$ of the leaking exhaled air evacuated from the subglottal region, similar to the function performed in the prior art via the suction lumen 14 and $CO_2$ monitor 9 in FIG. 1.

Figure 8:
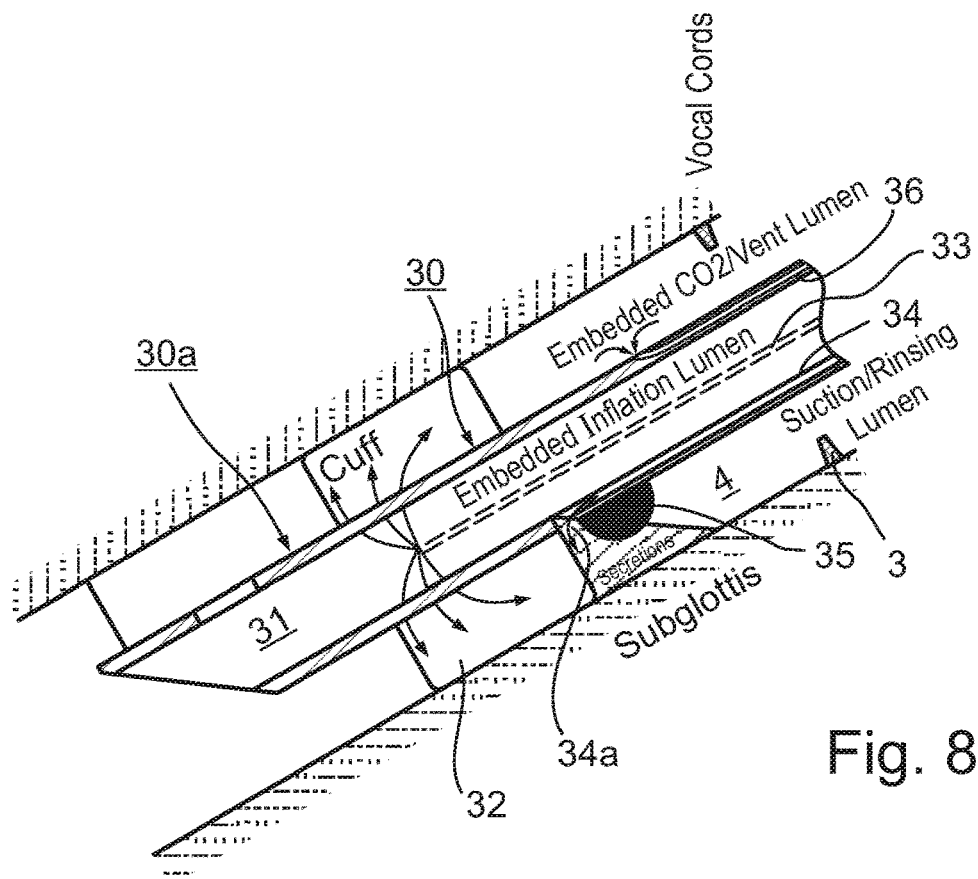
FIG. 8 illustrates a modification in the construction of the endotracheal tube of FIG. 6, particularly in the location of the protuberance preventing blockage of the suction inlet port.

The Embodiment of FIG. 8

FIG. 8 illustrates the distal end 30a of another endotracheal tube 30 constructed in accordance with the present invention, also including the basic elements described above with respect to FIGS. 6 and 7, mainly a main lumen 31, a cuff 32, an inflating lumen 33, and a suction lumen 34 having a suction inlet port 34a to be located in the subglottal region of the patient. In this case, the distal end of the endotracheal tube is formed with a protuberance 35 located adjacent to, but on the opposite side of the suction inlet port 24a such as to project radially outwardly of the outer surface of the endotracheal tube at the suction inlet port and to be effective to prevent blockage of the suction inlet port.

Endotracheal tube 30 illustrated in FIG. 8 also includes the venting lumen 36 integrally formed in the wall of the tube and having a port 36a to be located in the subglottal region 4 so as to prevent undue buildup of a negative pressure within that region during the mechanical ventilation of the patient. As will be described more particularly below, and as described above with respect to venting lumen 26 in FIGS. 6 and 7, venting lumen 36 in FIG. 8 may also be used, not only for venting the subglottal region to the atmosphere, but also for analyzing the composition, particularly the $CO_2$ content, of the exhaled air from the lungs leaking into that region, e.g., to control the pressure within cuff 32 in order to produce the desired tissue contact without damage to the surrounding tissue.

Figure 9:
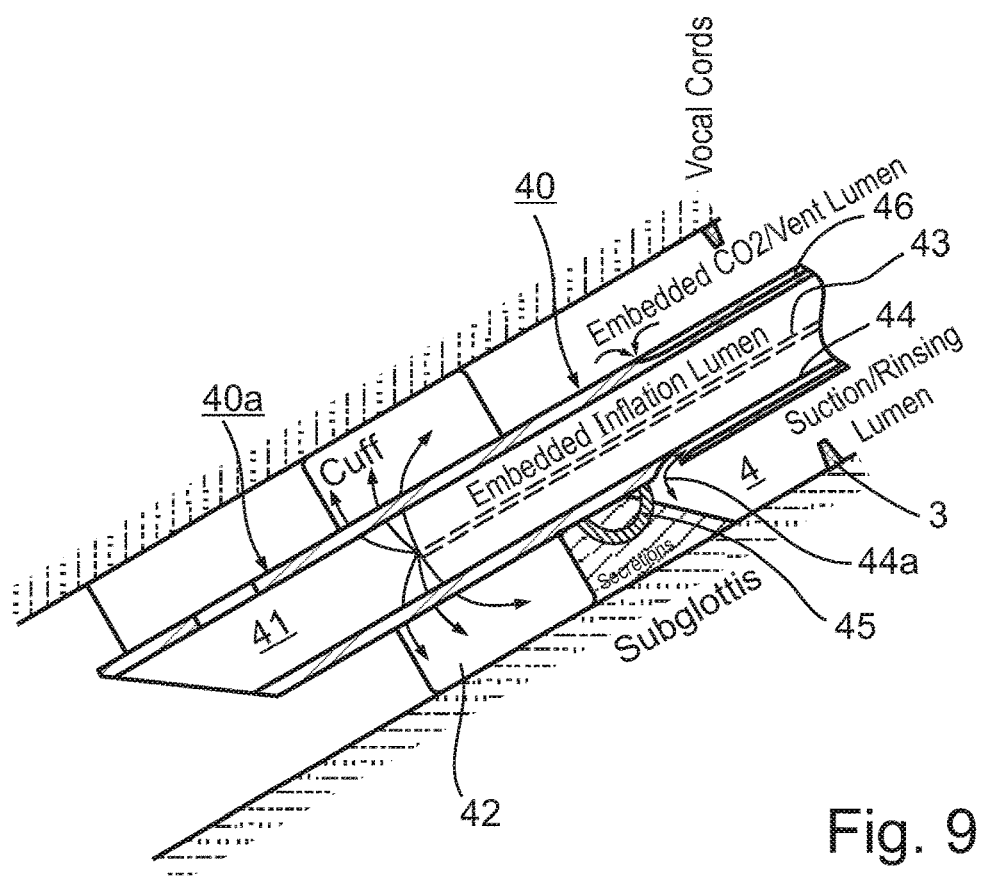
FIG. 9 illustrates a further modification in the construction of the endotracheal tube, particularly in the nature of the protuberance to prevent blockage of the suction inlet port.

The Embodiment of FIG. 9

FIG. 9 illustrates the distal end 40a of another endotracheal tube 40 constructed in accordance with the present invention of similar structure as described above with respect to FIG. 8. In endotracheal tube 40 of FIG. 9, however, the protuberance, thereby generally designated 45, is in the form of an inflatable element or balloon which, when inflated, projects radially outwardly of the outer surface of the tube at the suction inlet port, and thereby effectively prevents blockage of the suction inlet port. Inflatable element 45 may be of a blister configuration as shown, or of another configuration, e.g., annular configuration.

In all other respects, the endotracheal tube 40 illustrated in FIG. 9 is constructed and used in the same manner as described above with respect to FIG. 8.

Figure 10:
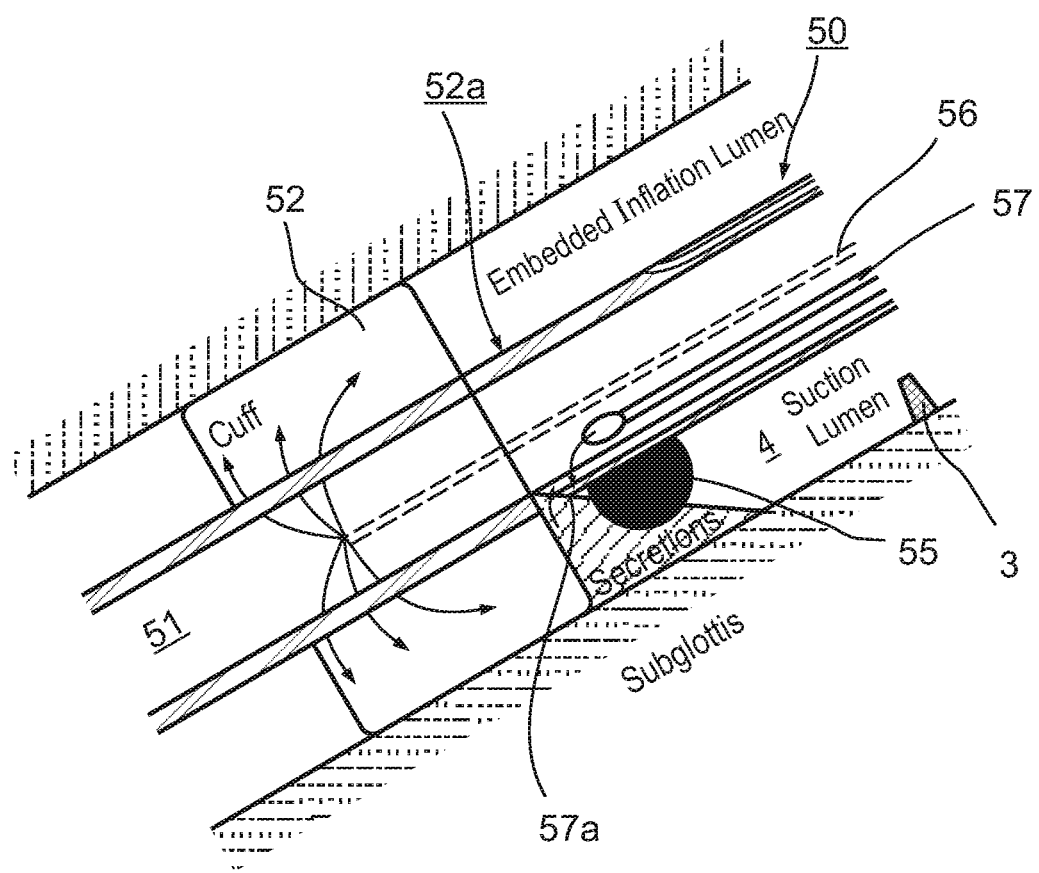
FIG. 10 illustrates a further modification in the construction of the endotracheal tube, to include separate suction and rinsing-fluid lumens.

The Embodiment of FIG. 10

FIG. 10 illustrates the distal end 50a of an endotracheal tube 50 constructed similar to that in FIGS. 6 and 7, except that the endotracheal tube of FIG. 10 further includes a rinsing lumen 57 for rinsing or irrigating the subglottal region 4. In such case, the rinsing lumen 57 has an outlet port 57a communicating with the subglottal region, preferably at the distal end thereof adjacent to the cuff 52.

By thus providing the endotracheal tube with a separate rinsing lumen 57, separate from the suction lumen 54, each lumen may be controlled to maximize its respective function, namely for rinsing the subglottal region via the rinsing lumen, and extracting secretions, as well as the rinsing fluid, from the subglottal region via the suction lumen. Where a separate rinsing lumen is not provided, as described above with respect to FIGS. 5-9, for example, the suction lumen would also be used for rinsing the subglottal region, and therefore would be controlled to perform its suction function and rinsing function alternatively, as will be described below with respect to FIGS. 11 and 12.

In all other respects, endotracheal tube 50 illustrated in FIG. 10 is constructed in the same manner as described above, to include a main lumen 51, cuff 52, inflating lumen 53, suction line 54 having an inlet port 54a, protuberance 55 and venting lumen 56.

Examples of Operation

Figure 11:
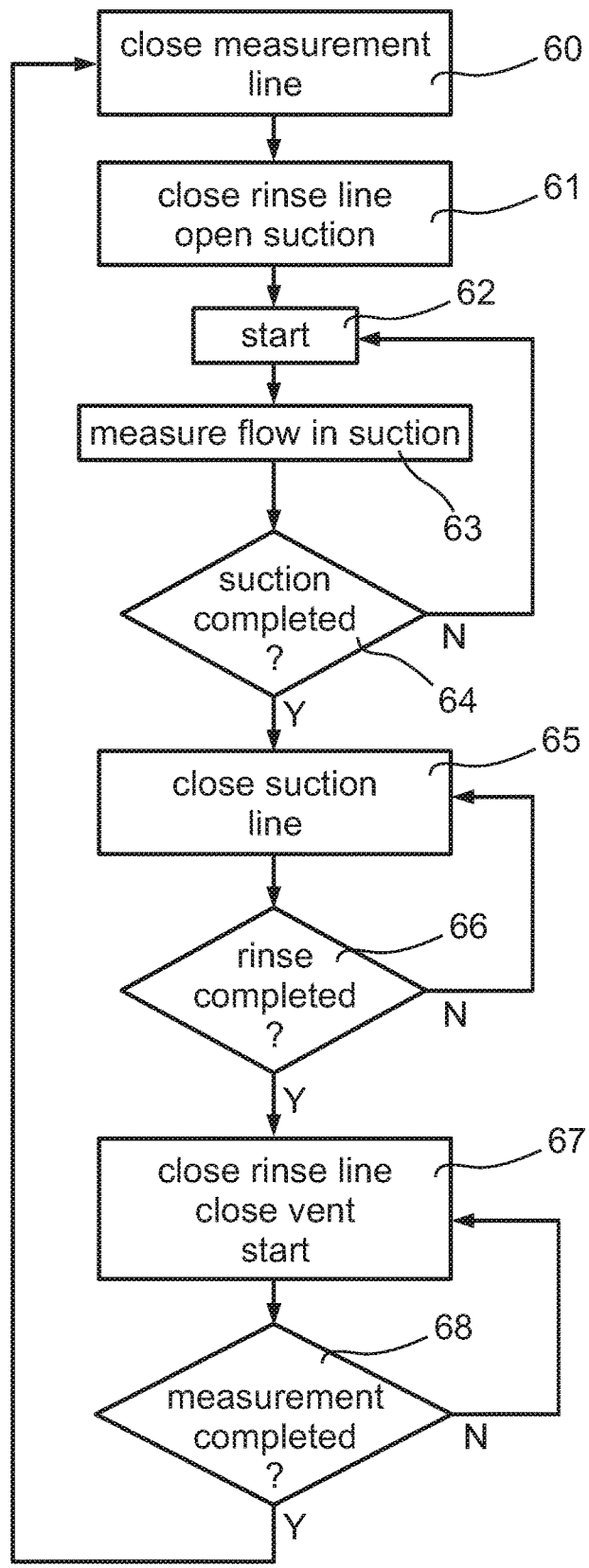
FIG. 11 is a flowchart illustrating the operation of an intubation system using the endotracheal tube of FIG. 7 or 8, for example.
Figure 12:
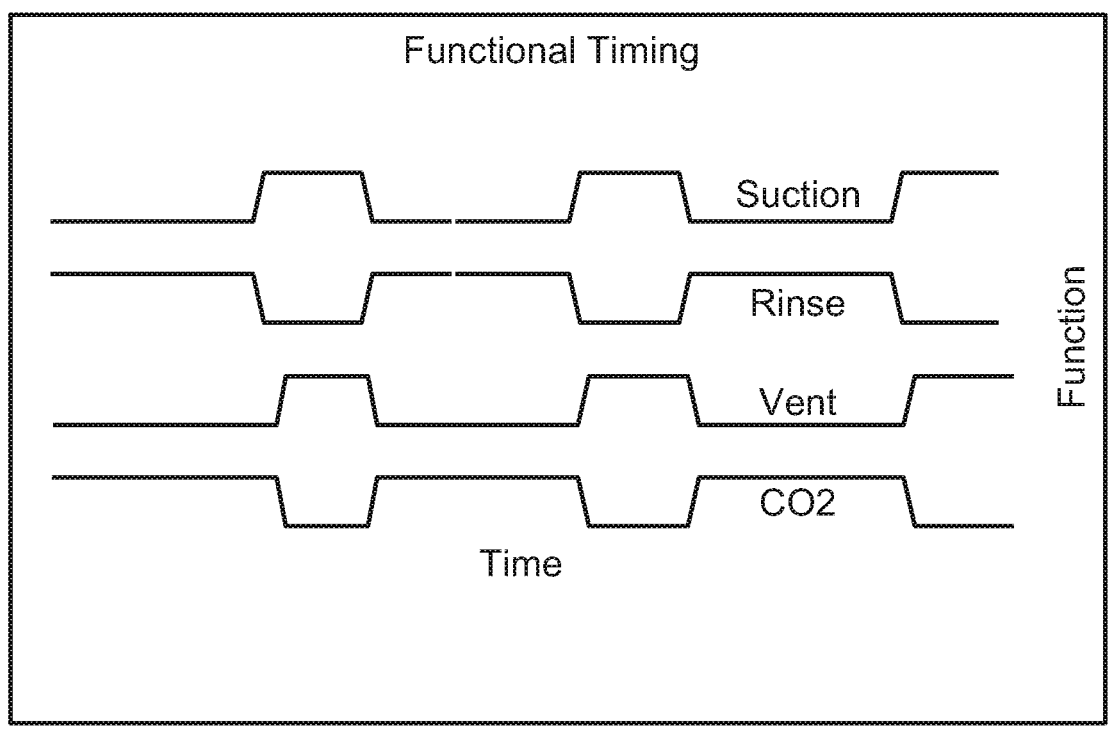
FIG. 12 is a timing diagram of the operation illustrated in the flowchart of FIG. 11.
Figure 13:
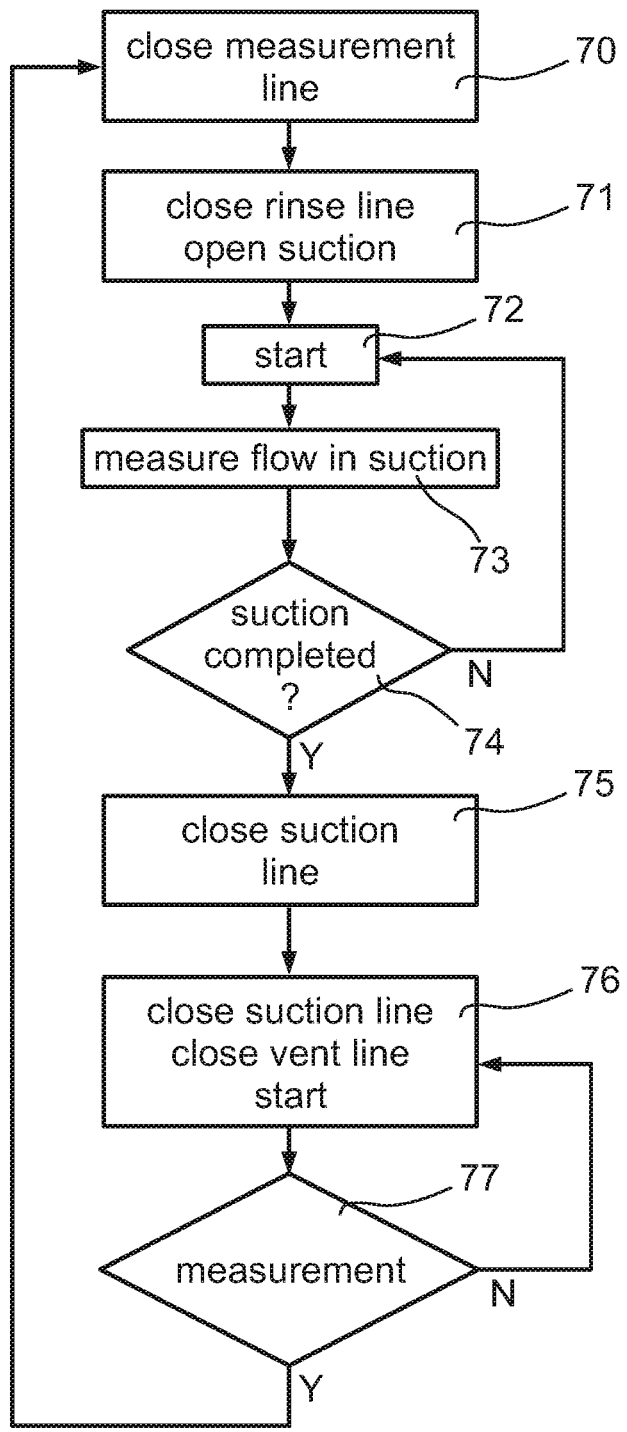
FIG. 13 is a flowchart illustrating the operation of an intubation system using the endotracheal tube of FIG. 10, having separate suction and rinsing-fluid lumens.
Figure 14:
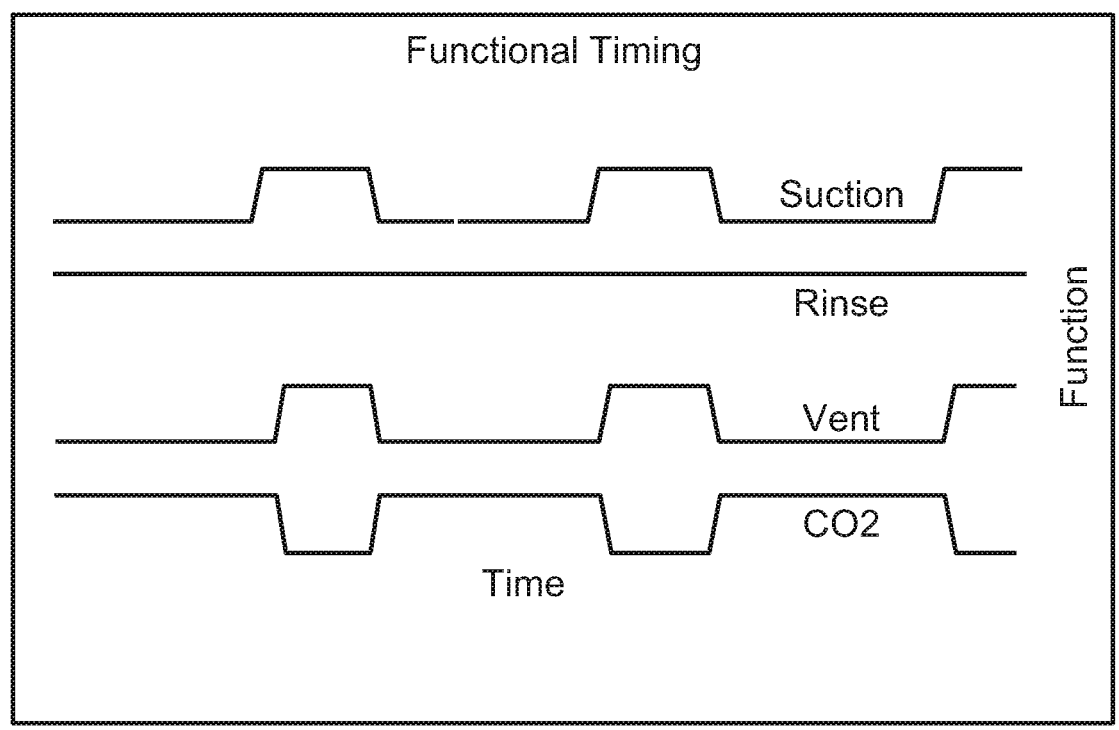
FIG. 14 is a timing diagram of the operation illustrated in the flowchart of FIG. 13.

The flowchart of FIG. 11, and timing diagram of FIG. 12, illustrate one example of operation of the above-described endotracheal tube illustrated in FIGS. 6-8, wherein there is no separate rinsing lumen, but rather the suction lumen is also used for rinsing. The corresponding flow chart and timing diagram of FIGS. 13 and 14 illustrate the corresponding operation of the endotracheal tube where a separate rinse lumen is provided, such as illustrated in FIG. 9. During both types of operations, the venting lumen e.g., 26, 36, 46, 56, is used intermittently, alternating for venting the subglottal region to the atmosphere, and for measuring the $CO_2$ content of the exhaled air leaking from the lungs and discharged from the subglottal region.

Thus, in the case where no separate rinsing lumen is provided (FIGS. 10 and 11), the suction lumen (e.g., 24) is also used for rinsing, and is therefore controlled to alternatingly perform its suction and rinsing functions as shown by blocks 60-68, FIG. 10. The venting lumen 26 is also used intermittently, for alternatingly performing its venting function and $CO_2$ measurement functions. In the example operation illustrated in FIGS. 11 and 12, it will be seen that the suction step is accompanied by the venting step to prevent the formation of underpressure. As noted by step 67 in FIG. 11, after the rinse line connected to suction lumen 24 has been closed, the venting lumen, e.g., 26, is used to enable completion of the measurement step 68.

FIGS. 13 and 14 are corresponding flow and timing diagrams illustrating the operation of the endotracheal tube where a separate rinse lumen is provided as in the case of rinse lumen 57 in FIG. 10, such that the rinse may be a continuous operation, whereas the suction is periodically applied in synchronism with the venting operation. As shown by blocks 70-77 in FIG. 13, and in the functional timing of FIG. 14, the $CO_2$ measuring operation, however, is performed in between the suction operations and is combined with the venting operations.

Figure 15:
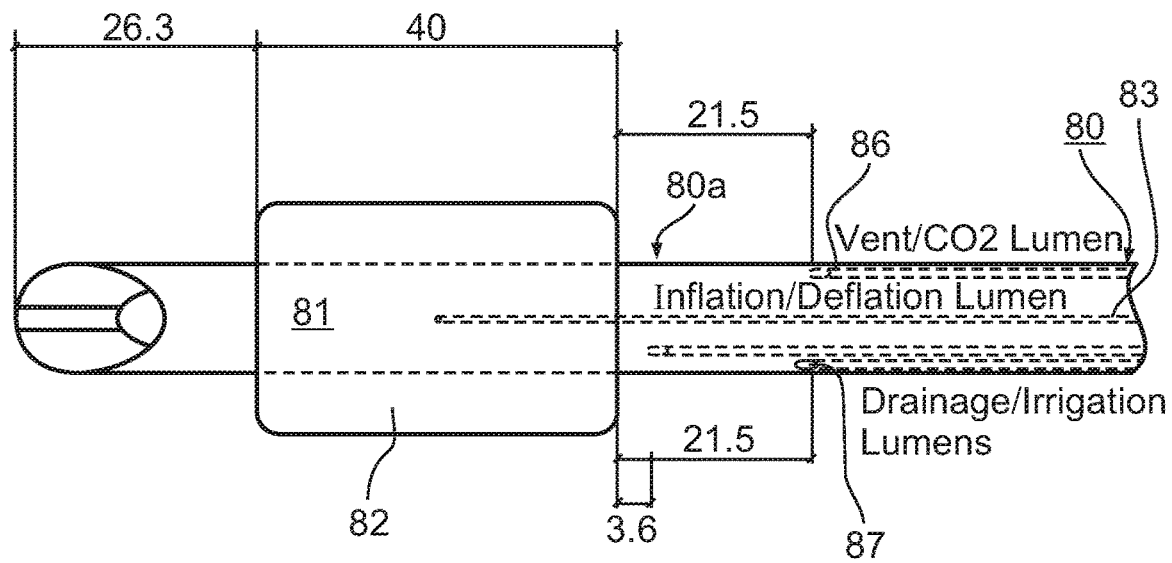
FIG. 15 is an elevational view illustrating another endotracheal tube constructed in accordance with the present invention.
Figure 16:
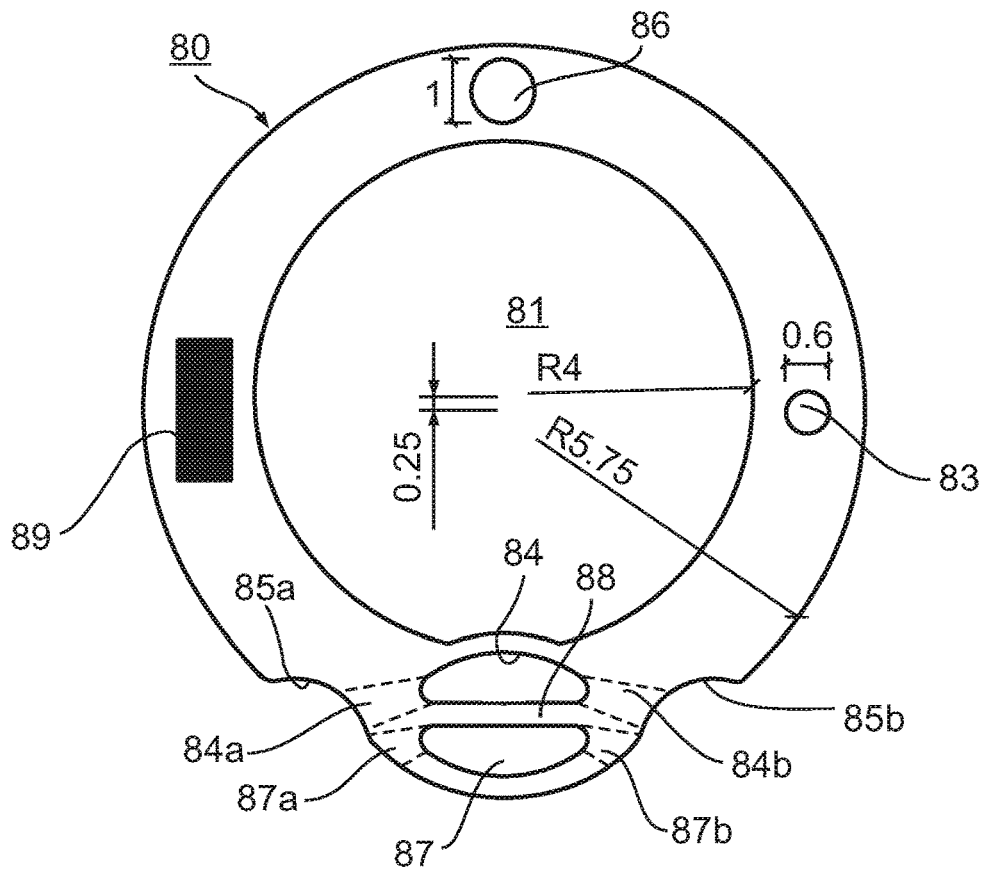
FIG. 16 is a transverse sectional view along line XVI-XVI of FIG. 15.

The Embodiment of FIGS. 15 and 16

FIGS. 15 and 16 illustrate an endotracheal tube to include all the foregoing lumens formed as passageways through the wall of the endotracheal tube, generally designated 80. Thus, endotracheal tube 80 includes a main lumen 81, a cuff 82 at the distal end 81a of the tube, an inflating lumen 83 for inflating/deflating the cuff, a suction lumen 84 for evacuating secretions and/or rinsing fluid from the subglottal region 4, a venting lumen 86 for venting the subglottal region to the atmosphere, and a rinsing lumen 87 for introducing a rinsing or irrigating fluid into the subglottal region.

It will be seen from FIG. 16 that the suction lumen 84 and rinsing lumen 87 are formed in the same side of the endotracheal tube in radial alignment, and are separated by a partition 88 integrally formed with the wall of the endotracheal tube.

It will also be seen from FIG. 16 that the outer surface of the endotracheal tube 80 is formed with a pair longitudinally-extending recesses 85a, 85b on opposite sides of the suction lumen 84 and rinsing lumen 87. Suction lumen 84 includes two suction inlet ports 84a, 84b, one in each of the two recesses 85a, 85b; similarly, rinsing lumen 87 includes two exit ports 87a, 87b, one in each of the recesses 85a, 85b, for introducing the rinsing fluid into the subglottal region.

It will thus be appreciated that the outer surface of the endotracheal tube 80 on opposite sides of the two recesses 85a, 85b, project outwardly of the two suction inlet ports 84a, 84b, and are therefore effective to prevent blockage of those ports either by the cuff 82, or by tracheal mucosal tissue of the patient, during a negative pressure condition in the suction lumen. It will also be appreciated that the two rinsing-fluid exit ports 87a and 87b of the rinsing lumen 87, also formed in recesses 85a and 85b adjacent to the suction inlet ports 84a, 84b, further reduce the possibility of blocking those inlet ports during the mechanical ventilation of the patient.

Endotracheal tube 80 further includes a radio opaque strip 89 integrally formed in the wall of the tube at the opposite side of the inflation lumen 83.

As one example, endotracheal tube 80 illustrated in FIGS. 15 and 16 may be made of silicon having an inner diameter of 8 mm, and an outer diameter of 11.5 mm. The Shore Hardness should be the maximum available. The outer diameter of the tube may be increased, but preferably not to exceed 12.5 mm. Other preferred dimensions appear on the drawings. It will be appreciated, however, that other materials could be used, e.g., polyvinyl chloride, and that the dimensions could be varied according to the requirements of any particular application.

While the invention has been described with respect to several preferred embodiments, it will be appreciated that these are set forth merely for purposes of example, and that many other variations, modifications and applications of the invention may be made.

What is claimed is:

1. A tracheal tube, comprising:
   a main lumen for delivering a breathing gas into a lung of a patient;
   a cuff, mounted at a distal end of the tracheal tube, to be located in the subglottal region of the patient;
   a cuff inflation lumen for inflating said cuff to form in the subglottal region a continuous volume which extends, within the subglottal region, from said cuff to the vocal cords of said patient; and
   at least three additional lumens, other than said main lumen and said cuff inflation lumen, configured for delivering liquid to said continuous volume, for suctioning liquid from said continuous volume, and for venting said continuous volume, wherein each of said at least three additional lumens ends with a port at said continuous volume and outside any cuff of the tracheal tube;
   wherein said delivering said liquid is via a rinsing port at said continuous volume, said suctioning of said liquid is via a suctioning port at said continuous volume, and said venting is via a venting port at said continuous volume, wherein said rinsing port, said suctioning port, and said venting port are separated from each other, and wherein lumens that end with said rinsing port, said suctioning port, and said venting port are separated from each other.

2. The tracheal tube according to claim 1, wherein said at least three additional lumens are arranged in a wall of said main lumen, such that one additional lumen is located at one side of said main lumen, and two additional lumens are located generally opposite to said one side of said main lumen.

3. The tracheal tube according to claim 2, wherein said one additional lumen is configured for said venting, and said two additional lumens are configured for said delivery of said liquid and said suctioning of said liquid.

4. The tracheal tube according to claim 1, wherein a proximal end of one of said at least three additional lumens is constructed for selective connection to a suction source or to a liquid source.

5. The tracheal tube according to claim 1, wherein a proximal end of one lumen of said at least three additional lumens is constructed for selective connection to the atmosphere or to an analyzing device for analyzing the composition of air leaking from the lungs into said subglottal region, and entering a respective port of said one lumen within said volume.

6. A system for use during ventilation of a patient through a trachea, the system comprising:
 a tracheal tube connectable to a mechanical ventilator, the tracheal tube having a main lumen for delivering a breathing gas from said mechanical ventilator into a lung of the patient; a cuff, mounted at a distal end of the tracheal tube, to be located in the subglottal region of the patient; a cuff inflation lumen for inflating said cuff, to form in the subglottal region a continuous volume which extends, within the subglottal region, from said cuff to the vocal cords of said patient; and at least three additional lumens, other than said main lumen and said cuff inflation lumen; and
 a controller configured for performing, via said at least three additional lumens:
 a delivery of liquid to said continuous volume, a suctioning of liquid from said continuous volume, and a venting said continuous volume;
 wherein each of said at least three additional lumens ends with a port at said continuous volume and outside any cuff of said tracheal tube;
 wherein said delivering said liquid is via a rinsing port at said continuous volume, said suctioning of said liquid is via a suctioning port at said continuous volume, and said venting is via a venting port at said continuous volume, wherein said rinsing port, said suctioning port, and said venting port are separated from each other, and wherein lumens that end with said rinsing port, said suctioning port, and said venting port are separated from each other.

7. A ventilation system, comprising a mechanical ventilator and the system of claim 6.

8. The system according to claim 6, wherein said at least three additional lumens are arranged in a wall of said main lumen, such that a first additional lumen is located at one side of said main lumen, and a second and a third additional lumens are located generally opposite to said one side of said main lumen.

9. The system according to claim 8, wherein said controller is configured for performing said venting via said first additional lumen, and for performing said delivery of said liquid and said suctioning of said liquid via said second and said third additional lumens.

10. The system according to claim 6, further comprising a suction source and a liquid source, and wherein said controller is configured for selectively connecting a proximal end of one of said at least three additional lumens to said suction source or to said liquid source.

11. The system according to claim 6, further comprising an analyzing device for analyzing the composition of air leaking from the lungs into said subglottal region, and wherein said controller is configured for selectively connecting a proximal end of one lumen of said at least three additional lumens to the atmosphere or to said analyzing device, wherein a respective port of said one lumen within said volume receives said leaking air.

12. The system according to claim 11, wherein said controller is configured for measuring flow during said suction, and connect said proximal end of said one of said at least three additional lumens to said analyzing device responsively to said measured flow.

13. The system according to claim 11, wherein said controller is configured for terminating said analysis and said delivery of said liquid prior to said suctioning of said liquid.

14. A method of ventilation a patient through a trachea, the method comprising:
 introducing a tracheal tube through the trachea, the tracheal tube having a main lumen; a cuff, mounted at a distal end of the tracheal tube, to be located in the subglottal region of the patient; a cuff inflation lumen for inflating said cuff to form in the subglottal region a continuous volume which extends, within the subglottal region, from said cuff to the vocal cords of said patient; and at least three additional lumens, other than said main lumen and said cuff inflation lumen;
 connecting a proximal end of the tracheal tube to a mechanical ventilator to deliver a breathing gas into a lung of the patient; and
 via said at least three additional lumens, delivering liquid to said continuous volume, suctioning of liquid from said continuous volume, and venting said continuous volume;
 wherein each of said at least three additional lumens ends with a port at said continuous volume and outside any cuff of said tracheal tube;
 wherein said delivering said liquid is via a rinsing port at said continuous volume, said suctioning of said liquid is via a suctioning port at said continuous volume, and said venting is via a venting port at said continuous volume, wherein said rinsing port, said suctioning port, and said venting port are separated from each other, and wherein lumens that end with said rinsing port, said suctioning port, and said venting port are separated from each other.

15. The method according to claim 14, wherein said at least three additional lumens are arranged in a wall of said main lumen, such that a first additional lumen is located at one side of said main lumen, and a second and a third additional lumens are located generally opposite to said one side of said main lumen.

16. The method according to claim 14, wherein said venting is via said first additional lumen, and said delivery of said liquid and said suctioning of said liquid are via said second and said third additional lumens.

17. The method according to claim 14, wherein said suctioning of said liquid is by a suction source and said delivery of said liquid is by a liquid source, and wherein the method comprises selectively connecting a proximal end of one of said at least three additional lumens to said suction source or to said liquid source.

18. The method according to claim 14, further comprising analyzing the composition of air leaking from the lungs and entering a respective port of one lumen of said at least three additional lumens within said volume.

19. The method according to claim 18, further comprising terminating said analysis and said delivery of said liquid prior to said suctioning of said liquid.

20. The method according to claim 14, further comprising measuring flow during said suctioning of said liquid, and connecting a proximal end of said one of said at least three additional lumens to an analyzing device for analyzing said composition of said air responsively to said measured flow.

* * * * *